(12) United States Patent
Sexton et al.

(10) Patent No.: US 8,957,387 B2
(45) Date of Patent: Feb. 17, 2015

(54) ABSORPTION PROBE FOR MEASURING DISSOLVED ORGANIC CARBON IN AN AQUEOUS SAMPLE

(75) Inventors: Brett Alexander Sexton, Balwyn North (AU); Michael John Best, Box Hill (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 13/806,701

(22) PCT Filed: Jun. 23, 2011

(86) PCT No.: PCT/AU2011/000779

§ 371 (c)(1),
(2), (4) Date: Mar. 5, 2013

(87) PCT Pub. No.: WO2011/160187

PCT Pub. Date: Dec. 29, 2011

(65) Prior Publication Data

US 2013/0153777 A1 Jun. 20, 2013

(30) Foreign Application Priority Data

Jun. 23, 2010 (AU) ................................. 2010902762

(51) Int. Cl.
*G01N 21/59* (2006.01)
*G01N 21/85* (2006.01)
(Continued)

(52) U.S. Cl.
CPC ............ *G01N 21/59* (2013.01); *G01N 21/8507* (2013.01); *G01N 33/1886* (2013.01); *C02F 2209/21* (2013.01); *G01N 21/33* (2013.01)
USPC ......................................................... 250/373

(58) Field of Classification Search
CPC .................................................... G01N 21/59
USPC .................................. 250/373, 459.1, 461.1
See application file for complete search history.

(56) References Cited

U.S. PATENT DOCUMENTS

| | | | | |
|---|---|---|---|---|
| 5,304,492 A | * | 4/1994 | Klinkhammer | 436/52 |
| 2009/0073436 A1 | * | 3/2009 | Higashi et al. | 356/326 |
| 2012/0183440 A1 | * | 7/2012 | Nakada et al. | 422/69 |

FOREIGN PATENT DOCUMENTS

| | | |
|---|---|---|
| EP | 0 494 524 A2 | 7/1992 |
| JP | 55-024671 A | 2/1980 |

(Continued)

OTHER PUBLICATIONS

Notification of Transmittal of the International Search Report and the Written Opinion of the International Searching Authority, or the Declaration, including an International Search Report, mailed Oct. 25, 2011 in connection with PCT International Application No. PCT/AU2011/000779, filed Jun. 23, 2011.
Written Opinion of the International Searching Authority, mailed Oct. 25, 2011 in connection with PCT International Application No. PCT/AU2011/000779, filed Jun. 23, 2011.

(Continued)

*Primary Examiner* — David Porta
*Assistant Examiner* — Faye Boosalis
(74) *Attorney, Agent, or Firm* — John P. White; Cooper & Dunham LLP (57) ABSTRACT

Some embodiments relate to an absorption probe for measuring an amount of dissolved organic carbon in an aqueous sample, the absorption probe comprising:
- a housing defining an analysis zone for the containment or passage of an aqueous sample;
- a light reflector disposed within said housing;
- an ultraviolet light emitting device disposed within said housing and operable to radiate ultraviolet light along an optical path that passes through the aqueous sample to impinge on said reflector; and
- a light detector disposed within said housing and operable to detect radiated light reflected from said reflector and to output a received signal from said detected reflected light, said received signal indicative of a measure of an amount of dissolved organic carbon in the aqueous sample.

20 Claims, 6 Drawing Sheets

(51) Int. Cl.
*G01N 33/18* (2006.01)
*G01N 21/33* (2006.01)

(56) References Cited

FOREIGN PATENT DOCUMENTS

| JP | 56-106143 A | 8/1981 |
| JP | 2002-277392 A | 9/2002 |
| SU | 1827596 A1 | 7/1993 |

OTHER PUBLICATIONS

Australian Patent Office International-Type Search Report, mailed Jul. 8, 2010 in connection with Australian Patent Application No. 2010902762, filed Jun. 23, 2010.

Official Communication dated Jun. 26, 2014 from the Chinese Patent Office, in connection with Chinese Patent Application No. 201180030009.1.

* cited by examiner

ABSORPTION PROBE FOR MEASURING DISSOLVED ORGANIC CARBON IN AN AQUEOUS SAMPLE

CROSS-REFERENCE TO RELATED APPLICATIONS

This application is a §371 national stage of PCT International Application No. PCT/AU2011/000779, filed Jun. 23, 2011, claiming priority of Australian Provisional Application No. 2010902762, filed Jun. 23, 2010, the contents of each of which are hereby incorporated by reference in their entirety.

TECHNICAL FIELD

Embodiments generally relate to absorption probes that may be used for measuring dissolved organic carbon in an aqueous sample.

BACKGROUND ART

Dissolved organic carbon (DOC) is generally defined as the organic matter that is able to pass through a filter, which removes material between 0.70 mm and 0.22 um in size. Determining the concentration of DOC in an aqueous sample, such as a sample of waste water or potable water, is important in diverse fields including pollution abatement and industrial processing situations.

Cost effective management of DOC is one of the key challenges facing today's water treatment industry. DOC has a major impact on treated water quality by for instance, acting as a food source for micro-organisms, reducing the capacity of membrane filtration by fouling, and influencing the taste and odour of water.

Techniques for the determination of DOC in an aqueous sample may involve the removal of inorganic carbon from the sample, oxidation of the organic carbon to carbon dioxide ($CO_2$), and quantitative determination of the resulting $CO_2$. DOC can be oxidized to $CO_2$ by wet chemical oxidation methods (e.g. persulfate oxidation), by high temperature combustion of the liquid or dried sample in the presence of an oxidizing or surface catalyst, or photochemically by UV-irradiation, with or without the presence of an oxidizing agent. Carbon dioxide is typically quantified by infrared absorption.

Such techniques usually require a combustion step at high temperatures (of the order of 500° C.). In addition, the instrumentation required for infrared absorption for the measurement of organic carbon in water is cumbersome hence laboratory based, and/or involves sophisticated and expensive equipment. Furthermore, the sample preparation protocol is lengthy.

It would, therefore, be desirable for a relatively inexpensive compact device which provides substantially real time measurements of the content of dissolved organic carbon in water or an aqueous solution, without the requirement of high temperatures or sophisticated instrumentation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

SUMMARY

Some embodiments relate to an absorption probe for measuring an amount of dissolved organic carbon in an aqueous sample, the absorption probe comprising:
   a housing defining an analysis zone for the containment or passage of an aqueous sample;
   a light reflector disposed within said housing;
   an ultraviolet light emitting device disposed within said housing and operable to radiate ultraviolet light along an optical path that passes through the aqueous sample to impinge on said reflector; and
   a light detector disposed within said housing and operable to detect radiated light reflected from said reflector and to output a received signal from said detected reflected light, said received signal indicative of a measure of an amount of dissolved organic carbon in the aqueous sample.

The light reflector may be back surface reflector or a front surface reflector. In an embodiment where the light reflector is a back surface reflector, aluminium, silver, a metal with a high UV reflectance or a dielectric reflector layer may be deposited on an ultraviolet transmitting quartz disc or UV transmitting glass. Preferably, UV transmitting glasses include sapphire or high fluoride content glasses.

In an embodiment where the light reflector is a front surface reflector, aluminium, silver, a metal with a high UV reflectance or a dielectric reflector layer is deposited on a layer of plate glass, common glass or a non-ultraviolet transmitting flat substrate. Preferably, the front surface reflector further comprises a protective overcoat of silicon dioxide or magnesium fluoride when a metal deposit such as aluminium or silver is used. Non-ultraviolet transmitting flat substrates may comprise injection moulded polymers such as polycarbonate or PMMA or metals such as polished stainless steel or aluminium.

In one embodiment the light reflector is a mirror.

The housing may comprise a first member detachably connected to a second member. The second member may comprise a sheath which engages with an outer surface of said first member. The sheath may slidably engage with the outer surface of said first member. In another embodiment, the first member may comprise a sheath which slidably engages the outer surface of the second member. Furthermore, the first and second member may be attached by a screw thread mechanism where their separation is conducted by rotation relative to each other. The second member may comprise a cavity which defines the analysis zone. The first member, and/or the second member, may be provided with a limit means to limit the extent of slidability or extension of the second member over the first member, and which therefore defines the path length through the analysis zone. This feature has the advantage of adjustment of the path length and the resultant response of the probe.

The analysis zone may have a passageway through it to allow transport of the aqueous sample through the analysis zone. A wall of the second member surrounding the cavity may have two or more apertures configured to permit circulation of the sample when at least a portion of the absorption probe is immersed in a body of water. In such a configuration the probe may be hand held and readily portable.

Optionally a wall of the second member surrounding the cavity may have engagement means to engage the output of a faucet. Such an embodiment facilitates use of the absorption probe in an in-line or flow through application. In another embodiment, the engagement means for attachment to a faucet may be incorporated in a sheath which is extended from the first member, with the second member slidably or rotationally connected to the first member.

The light reflector and light detector may be disposed proximate a first end of the first member.

The first end of the first member may be capped by an ultraviolet radiation transparent element. The ultraviolet radiation transparent element may comprise quartz. Optionally the ultraviolet radiation transparent element may comprise sapphire.

The absorption probe may further comprise a power source operable to supply energy to said absorption probe.

The absorption probe may include a signal processing unit operable to process said received signal to calculate a measure of the amount of dissolved organic carbon in the aqueous sample according to Beer's-Lamberts Law.

The signal processing unit may be a physically separate unit from the housing. In such an example the signal processing unit may be in signal communication with the light detector and light source.

The ultraviolet light emitting device may be broad spectrum or may be monochromatic. The ultraviolet light emitting device may be operable to emit light in the wavelength band of approximately 200 nm to 400 nm. The ultraviolet light emitting device may be operable to emit light in the wavelength band of approximately 170 nm to 280 nm, or preferably 200 nm to 270 nm. The ultraviolet light emitting device may comprise a light emitting diode operable to emit light at approximately 253 nm, 254 nm, 255 nm, 256 nm or 257 nm.

The absorption probe may further comprise a collimator to collimate the ultraviolet light radiated from the light emitting diode.

Optionally, the ultraviolet light emitting device may comprise a low pressure mercury lamp. UV absorbance at around about 254 nm is a convenient measure because it corresponds to the clearly defined spectral line of a low pressure mercury lamp (253.7 nm). If a low pressure mercury lamp is used then the absorption probe may further comprise an interference filter capable of selecting the ultraviolet component and substantially rejecting the visible light component.

The use of the term aqueous includes reference to potable water, waste water, water in streams, rivers and dams, runoff water from homes and domestic storage tanks. The readings are referenced against de-ionized water or distilled water containing no dissolved organic carbon as a standard.

The signal processing unit may include or be in communication with a memory to which is stored a measure $I_o$ of the intensity of the light as measured through a sample of distilled or deionised water containing substantially no carbon.

BRIEF DESCRIPTION OF THE DRAWINGS

In order that the invention may more readily be understood, reference now is directed to the accompanying drawings, in which like numbers refer to like elements and in which.

DETAILED DESCRIPTION

FIGS. 1, 3, 4 and 6 illustrate a first embodiment of a hand-held portable absorption probe 100 for measuring an amount of dissolved organic carbon in an aqueous sample.

The hand-held absorption probe 100 measures the transmission or absorbance of water at a wavelength of approximately 255 nm, which is an industry standard for detection of dissolved organic carbon (DOC) and "aromatic" dissolved carbon. Waters contaminated with dissolved organic carbon have a broad absorption spectrum which extends from below 250 nm to 400 nm. The absorption of light in these waters increases significantly as the wavelength is reduced from 400 to 250 nm. UV 254 is selected as an industry standard because traditionally a mercury discharge lamp is used to generate the UV light where mercury has a strong emission at 253.7 nm. The exact wavelength is not critical to the analysis, but preferably a wavelength close to 254-255 nm is chosen to maximise the sensitivity.

The absorption probe 100 comprises a housing made up of a first member 105 and a second member 110. Each of the first and second members comprise hollow cylinders which are machined from acetal polymer (Delrin). Alternatively, other materials such as machinable polymers, metals such as aluminium alloy, stainless steel or injection mouldable polymers can be used for construction, where resistance to corrosion by immersion in water is desirable. A first end of the first member 105 is capped with an ultraviolet radiation transparent element in the form of a quartz window 140. Situated behind the quartz window 140 is an ultraviolet light emitting device (UV Led) in the form of a UV light emitting diode 145 operable to radiate light at approximately 254-255 nm. A quartz ball lens 150 is provided to collimate the radiation emitted from the UVLed 145.

A light detector in the form of a UV-sensitive photodiode 155 is also situated behind the quartz window 140.

Figure 9:
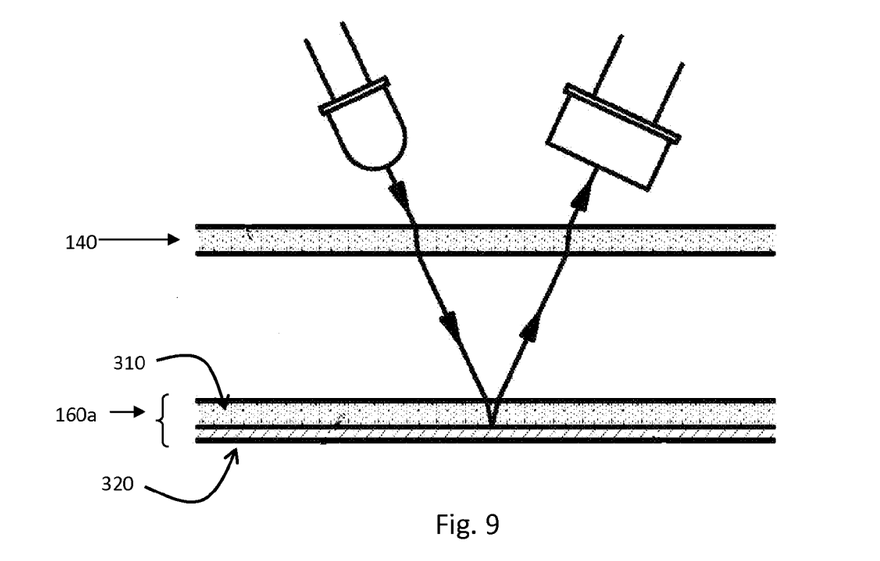
FIG. 9 is a schematic illustration of the sensor having a rear surface reflective mirror.

Contained within a first end of the second member 110 is a light reflector 160. The light reflector 160 can either be a back surface reflector 160a as illustrated with reference to FIG. 9, or a front surface reflector 160b as illustrated with reference to FIG. 10. In the example of the back surface reflector 160a, an ultraviolet-transparent quartz disc 310 is provided with a rear aluminium, silver, a metal with a high UV reflectance or a dielectric reflector layer 320 deposited thereon. Alternatively, 310 could comprise of a suitable UV transmitting glass. Examples of suitable UV transmitting glasses include sapphire or high fluoride content glasses.

Figure 10:
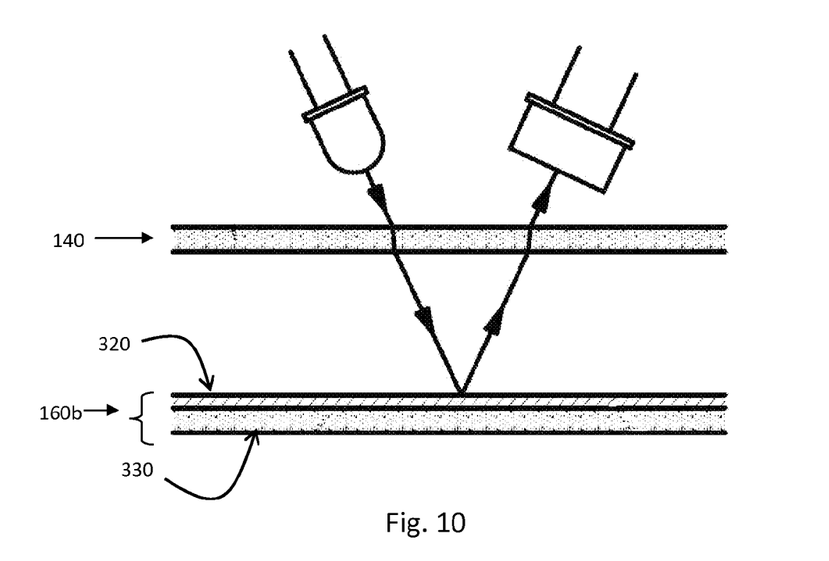
FIG. 10 is a schematic illustration of the sensor having a front surface reflective mirror.

In the example of the front surface reflector 160b, a first layer of plate glass 330 or other non-UV transmitting material is provided and deposited thereon is a layer of aluminium coating, silver, a metal with a high UV reflectance or a dielectric reflector layer 320. Alternatively, 330 could comprise of common glass or non-ultraviolet transmitting flat substrate. Examples of non-ultraviolet transmitting flat substrate include injection moulded polymers such as polycarbonate or PMMA, or metals such as polished stainless steel or aluminium. If a metal coating such as aluminium or silver is used, a thin protective overcoat of silicon dioxide (not shown) may be applied to the front surface to prevent corrosion. The aluminium mirror coating is applied to the glass rear or front surface by vacuum sputtering or electron beam or thermal evaporation to a thickness of 100-200 nm. It may be protected on the front surface by application of a thin layer of silicon oxide, which is electron beam evaporated in high vacuum. Other materials such as magnesium fluoride may also be used as a protective layer to prevent water corrosion of the thin film. If a rear surface reflector is used, it may be sealed from contact with water on the rear surface by enclosing it in a plastic housing or applying a lacquer layer. Alternatively, for the UV reflective coating, multilayer dielectric coatings may be used to substitute for protected metal coatings.

Referring back to FIGS. 1, 3, 4 and 6, formed within a lower portion of the wall of the second member 110 are six apertures 135 (of which only three are shown) configured to permit circulation of an aqueous sample when at least a portion of the absorption probe 100 is immersed in a body of water which is subject to testing.

The second end of the second member 110 forms a sheath 115 and the diameter of the first member 105 is less than that of at least the sheath 115 of the second member 110 to enable the second member 110 to slide over the outer surface of the first member 105. A limit means in the form of a stop pin 120 projects from the outer wall of the first member 105 and a lip 125 of the sheath 115 abuts with the stop pin 120. The location of the stop pin 120 defines the path length of the analysis zone 130 subsequently formed. The UV light emitting diode 145 is angled with respect to the UV-sensitive photodiode 155 to allow the reflected radiated light to impinge on the photodiode 155 after transiting the water, and to optimise the signal extracted from the photodiode 155 when the lip 125 of the sheath 115 optionally abuts with the stop pin 120.

In use, the lip of the sheath 115 need not abut the stop pin 120, and the distance of the sheath 115 relative to the stop pin 120 may be varied to adjust the sensitivity of the instrument.

The first member 105 and second member 110 are releasably connectable with one another such that when they are connected with one another they form a compact hand-held absorption probe. The separability of the first member 105 from the second member 110 facilitates cleaning of the light reflector 160, quartz window 140, as well as other surfaces exposed to the aqueous sample.

Figure 1:
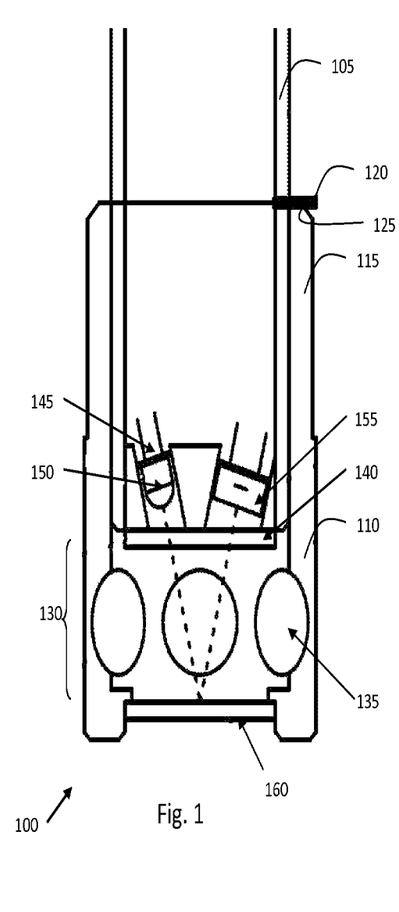
FIG. 1 is a diagrammatic sectional view of a first embodiment of an absorption probe.
Figure 2:
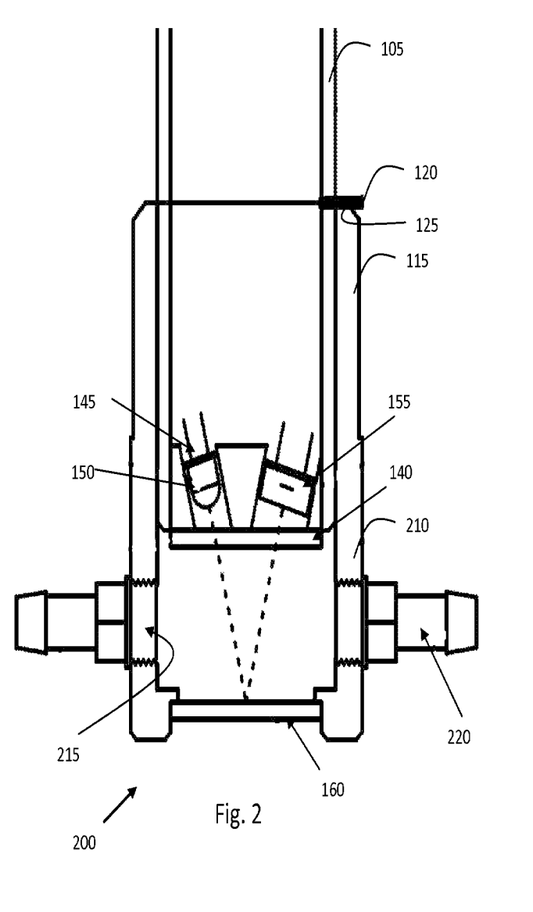
FIG. 2 is a diagrammatic sectional view of a second embodiment of an absorption probe.
Figure 3:
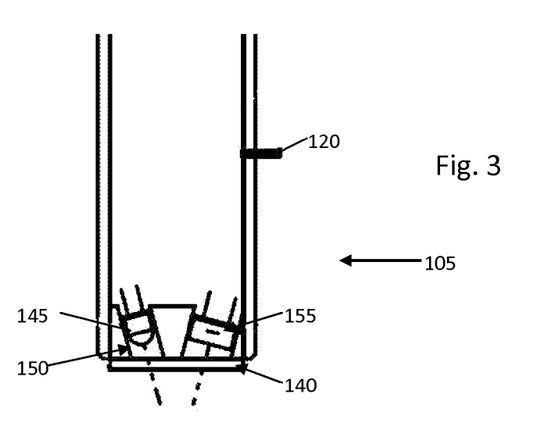
FIG. 3 is a diagrammatic sectional view of the first member of either the first embodiment illustrated in FIG. 1, or the second embodiment illustrated in FIG. 2.
Figure 4:
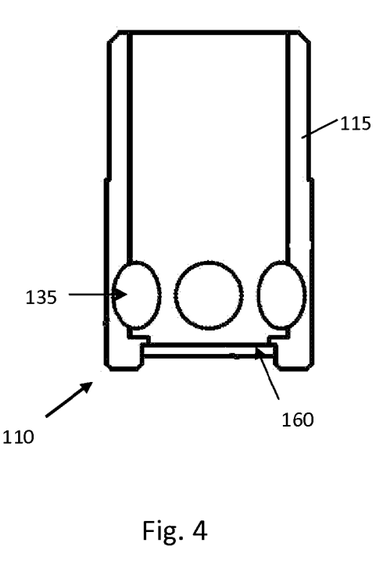
FIG. 4 is a diagrammatic sectional view of the second member of the first embodiment illustrated in FIG. 1.
Figure 5:
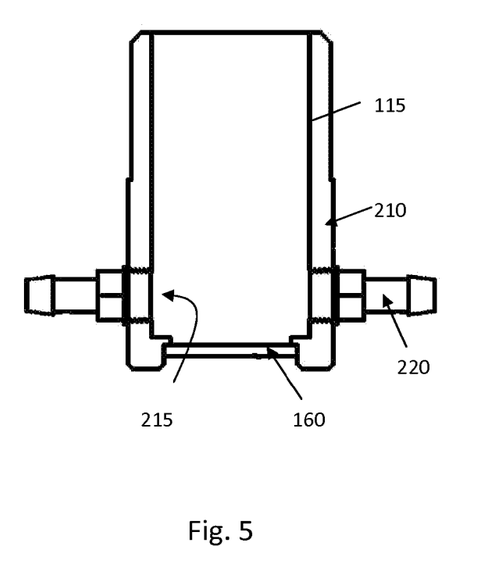
FIG. 5 is a diagrammatic sectional view of the second member of the second embodiment illustrated in FIG. 2.
Figures 6, 7:
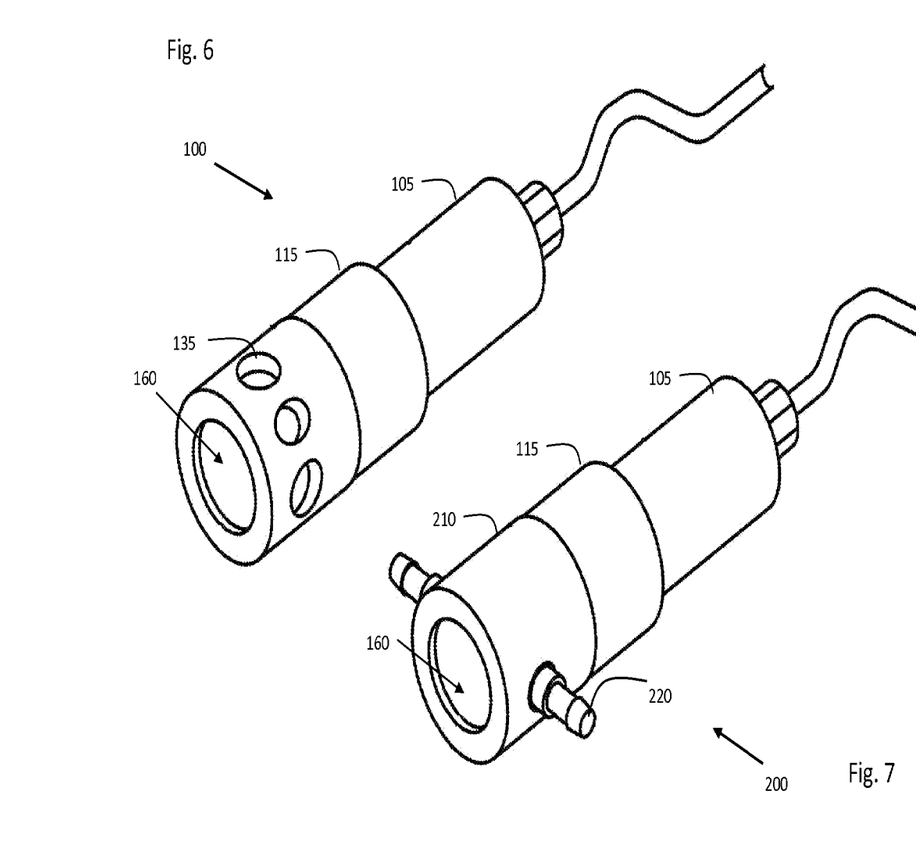
FIG. 6 is a perspective view of an assembled probe in accordance with the first embodiment illustrated in FIG. 1.
FIG. 7 is a perspective view of an assembled probe in accordance with the second embodiment illustrated in FIG. 2.

The absorption probe 100 comprises a container (not shown) containing a signal processing unit and memory. The container is physically separate from the housing yet is in signal communication with the light detector and light-emitting diode. The signal processing unit supplies power to the LED 145, processes signals received from the UV-sensitive photodiode 155 and calculates a measure of an amount of dissolved organic carbon in the aqueous sample according to Beer's-Lamberts Law.

To calculate a measure of the amount of dissolved organic carbon in the aqueous sample, a measure of the transmission of light in substantially pure distilled or de-ionised water containing no dissolved organic carbon $I_o$ is required. The reference water sample is preferably 100% deionized (DI) water. This can either be obtained in real-time, prior to testing the aqueous sample whereafter the measured value $I_0$ is stored to memory. Alternatively $I_0$ may have been previously obtained and stored to memory for later use.

At least the portion of the absorption probe 100 containing the analysis zone is then immersed in the body of water being tested. UV light emitting diode 145 is pulsed at a particular frequency and the reflected light is sensed by the UV-sensitive photodiode 155 as an AC signal. The signal is amplified by a pre-amplifier before being passed through a band pass filter to remove unwanted noise. The filtered signal is then rectified and further filtered to produce an analog output voltage which is proportional to the transmission intensity $I_T$. The circuitry should preferably be designed to minimise interference from stray visible light from fluorescent lights or other sources.

Absorption of ultraviolet light is measured and typically as percent transmittance, T, where $T=100 \times I_T/I_o$. For analysis, transmittance is converted to absorbance, A, where $A=\log 10(1/T)$. Quantitative measurements are possible based upon the fundamental relationship between absorbance, absorptivity, and concentration expressed by Beer's Law. See, e.g., G. W. Ewing, Instrumental Methods of Chemical Analysis, 5th ed., pp. 32-35 (McGraw-Hill, New York, 1985) incorporated herein by reference. Since absorptivity is an inherent property of a chemical compound, it is a constant for a given compound at a given wavelength. Since absorbance is directly proportional to concentration, differences in absorbance (e.g., between that of the sample and that of the reference) are most readily observable when sample concentration is high relative to the reference sample. Therefore, the sensitivity of the method of the invention depends on the use of a sample of sufficient size so that sample absorbances are observable after reference sample absorbances are subtracted out but not so great so as to exceed the capacity of the detector.

With reference to FIGS. 2, 3, 5 and 7, a second embodiment of a hand-held absorption probe 200 is illustrated.

The absorption probe 200 in the second embodiment is suitable for an in-line or flow through application where the probe 200 is attached, for instance, to a faucet. With the exception of the second member 210, all remaining components of the flow through application absorption probe 200 are identical to the hand held probe 100 and will not be repeated here.

Formed within a lower portion of the wall of the second member are a pair of apertures 215. An engagement means 220 is affixed to each of the apertures 215, such means being operable to engage the output of a faucet. As with the first embodiment, the second end of the second member 210 forms a sheath 115 which slides over the outer surface of the first member 105 and enables releasable engagement, although it should be appreciated that the probe of the second embodiment 200 will be subject to much higher fluid flows and therefore pressure than the first embodiment that the engagement means 220 will be significantly more fluid tight. As with the first embodiment, a light reflector 160 is contained within a first end of the second member 210 and a limit means in the form of a stop pin 120 projects from the outer wall of the first member 105 and a lip 125 of the sheath 115 abuts with the stop pin 120 to optimise the path length.

Figure 8:
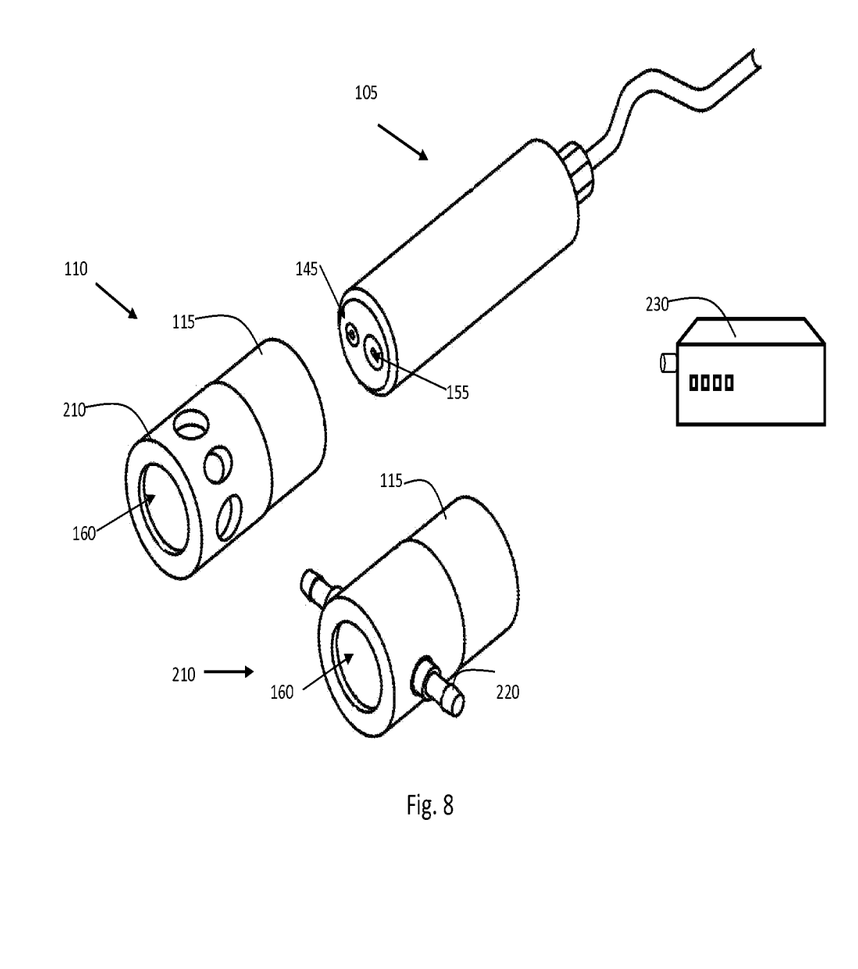
FIG. 8 is a perspective view of a kit.

FIG. 8 illustrates a perspective view of a kit comprising a first member 105, a pair of second members 110 and 210 and a container 230 containing a signal processing unit and in built memory.

Figure 11:
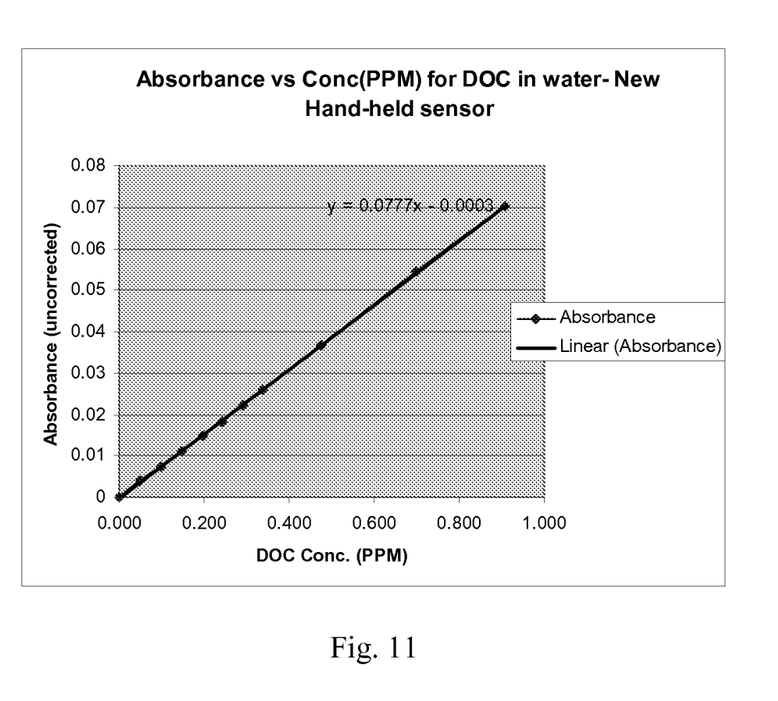
FIG. 11 is a graph illustrating a calibration curve for the new sensor showing good sensitivity down to low PPB ranges.
Figure 12:
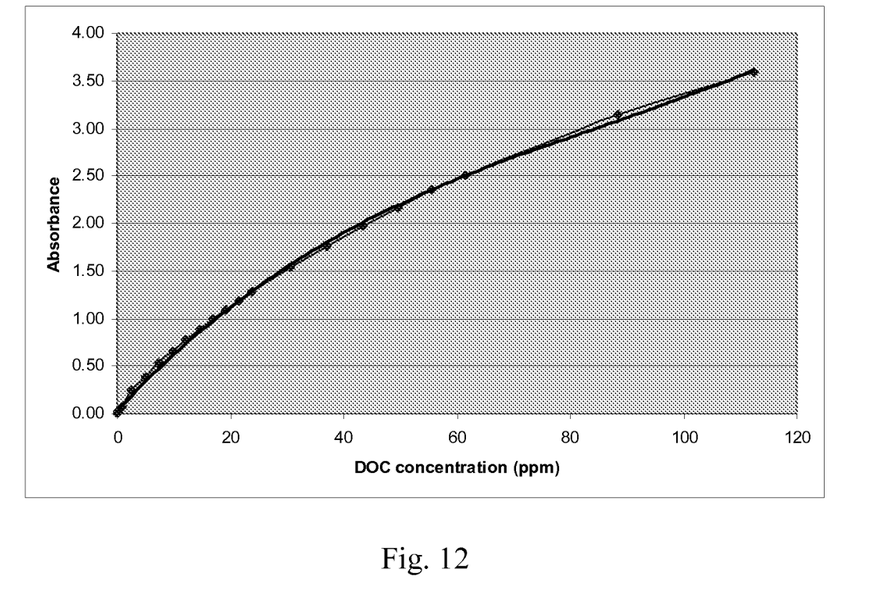
FIG. 12 is a graph illustrating sensor response at higher concentrations of dissolved organic carbon.

FIG. 11 is a graph illustrating a calibration curve for the absorption probe 100 which exhibits very good sensitivity down to low parts per billion (PPB) ranges. FIG. 12 is a graph illustrating the response of the absorption probe 100 at higher concentrations of dissolved organic carbon. In both situations the absorption probe 100 was calibrated with potassium hydrogen phthalate (KHP) at various concentrations. As is evident, the absorption probe 100 exhibits a linear or smooth correlation between absorbance and concentration of DOC which facilitates calibration. Table 1 shows measurements of DOC in potable and recycled waters taken with both the hand held sensor and a commercial bench UV-VIS spectrophotometer. A good correlation of the readings is found demonstrating the utility of the instrument in discriminating between different type of potable and recycled waters.

TABLE 1

Concentration comparison of recycled and potable waters

| Sample | Hand-held sensor Calculated from standard additions curve Dissolved organic carbon (PPM) | Varian Cary UV Spectrophotometer Dissolved organic carbon (PPM) |
|---|---|---|
| Recycled water | 18.7 | 23.1 |
| Laboratory tap 1 | 1.7 | 2.0 |
| Drinking fountain | 0.25 | <0.30 |
| Laboratory Tap 2 | 3.06 | 3.00 |

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

For instance, the foregoing description describes the ability of the second member 110 to slide over the outer surface of the first member 105 and a stop pin 120 which projects from the outer wall of the first member 105, in alternative embodiments, the first and second member may be engaged by a screw thread mechanism where the separation of the members is adjusted by rotating one against the other. In another embodiment, the stop pin 120 can be replaced by a locking screw or other clamp mechanism to fix the distance between the two members.

Numerous variations and/or modifications may be made to the described embodiments without departing from the scope of the invention as broadly described. The present embodiments are, therefore, to be considered in all respects as illustrative and not restrictive.

The invention claimed is:

1. A handheld absorption probe to measure an amount of dissolved organic carbon in an aqueous sample, the absorption probe comprising:
   a housing defining an analysis zone for the containment or passage of an aqueous sample;
   a light reflector disposed within said housing;
   an ultraviolet light emitting device disposed within said housing and operable to radiate ultraviolet light along an optical path that passes through the aqueous sample to impinge on said reflector; and
   a light detector disposed within said housing and operable to detect radiated light reflected from said reflector and to output a received signal from said detected reflected light, said received signal indicative of a measure of an amount of dissolved organic carbon in the aqueous sample.

2. An absorption probe according to claim 1, wherein the light reflector is one of a back surface reflector or a front surface reflector.

3. An absorption probe according to claim 2, wherein the light reflector is a back surface reflector comprising aluminium, silver, a metal with a high UV reflectance, or a dielectric reflector layer deposited on a ultraviolet transmitting quartz disc or a UV transmitting glass.

4. An absorption probe according to claim 3, wherein a protective overcoat of silicon dioxide or magnesium fluoride is applied to the deposited aluminium or silver.

5. An absorption probe according to claim 2, wherein the light reflector is a front surface reflector comprising aluminium, silver, a metal with a high UV reflectance or a dielectric reflector layer deposited on a layer of plate glass, common glass or non-ultraviolet transmitting flat substrate.

6. An absorption probe according to claim 5, wherein a protective overcoat of silicon dioxide or magnesium fluoride is applied to the deposited aluminium or silver.

7. An absorption probe according to claim 1, wherein the light reflector is a mirror.

8. An absorption probe according to claim 1, wherein the housing comprises a first member within which is housed the ultraviolet light emitting device and the light detector and a second member within which is housed the light reflector.

9. An absorption probe according to claim 8, wherein the light reflector and light detector are disposed proximate a first end of the first member, and the first end of the first member is capped with an ultraviolet radiation transparent element.

10. An absorption probe according to claim 9 further comprising a collimator to collimate the ultraviolet light radiated from the light emitting diode.

11. An absorption probe according to claim 8 further comprising a collimator to collimate the ultraviolet light radiated from the light emitting diode.

12. An absorption probe according to claim 8, wherein the first member is detachably connectable to the second member.

13. An absorption probe according to claim 12, wherein an end of the second member slidably or rotationally engages with a surface of said first member to connect the respective members together.

14. An absorption probe according to claim 13, wherein the first member is provided with a limit means to limit the extent of engagement with the second member.

15. An absorption probe according to claim 8, wherein the second member has a passageway through it to enable transport of the aqueous sample through the analysis zone.

16. An absorption probe according to claim 15, wherein a wall of the second member has two or more apertures configured to permit circulation of the aqueous sample when at least a portion of the absorption probe is immersed in a body of water.

17. An absorption probe according to claim 16, wherein a wall of the first or second member surrounding the cavity has engagement means to engage the output of a faucet.

18. An absorption probe according to claim 1 further comprising a signal processing unit operable to process said received signal to calculate a measure of an amount of dissolved organic carbon in the aqueous sample according to Beer's-Lamberts Law.

19. An absorption probe according to claim 18, where the signal processing unit is a physically separate unit from the housing and the signal processing unit is in signal communication with the light detector.

20. An absorption probe according to claim 19, wherein the signal processing unit stores a measure of the transmission $I_0$ of ultraviolet light in substantially pure distilled or de-ionised water containing no dissolved organic carbon.

* * * * *